(12) United States Patent
Ivachtchenko et al.

(10) Patent No.: US 10,738,049 B2
(45) Date of Patent: Aug. 11, 2020

(54) N-{3-[3-CYCLOPROPYL-5-(2-FLUORO-4-IODOPHENYLAMINO)-6,8-DIMETHYL-2,4,7-TRIOXO-3,4,6,7-TETRAHYDRO-2H-PYRIDO[4,3-D]PYRIMIDIN-1-YL]-PHENYL}-CYCLOPROPANECARBOXAMIDE DIMETHYL SULFOXIDE SOLVATE AS AN MEK1/2 INHIBITOR

(71) Applicants: R-PHARM JOINT STOCK COMPANY (R-PHARM, JSC), Moscow (RU); Alexey Evgenievich Repik, Yaroslavl (RU)

(72) Inventors: Alexandre Vasilievich Ivachtchenko, Hallandale Beach, FL (US); Alexey Evgenievich Repik, Yaroslavl (RU); Vasily Gennadievich Ignatiev, Moscow (RU); Mikhail Airatovich Chafeev, Moscow (RU)

(73) Assignee: R-PHARM JOINT STOCK COMPANY (R-PHARM, JSC), Moscow (RU)

( * ) Notice: Subject to any disclaimer, the term of this patent is extended or adjusted under 35 U.S.C. 154(b) by 0 days.

(21) Appl. No.: 16/340,874

(22) PCT Filed: Dec. 12, 2016

(86) PCT No.: PCT/RU2016/000862
§ 371 (c)(1),
(2) Date: Apr. 10, 2019

(87) PCT Pub. No.: WO2018/070900
PCT Pub. Date: Apr. 19, 2018

(65) Prior Publication Data
US 2019/0233415 A1 Aug. 1, 2019

(30) Foreign Application Priority Data
Oct. 10, 2016 (RU) .................. 2016139641

(51) Int. Cl.
*A61K 31/519* (2006.01)
*C07D 471/04* (2006.01)
*A61P 35/00* (2006.01)

(52) U.S. Cl.
CPC ............ *C07D 471/04* (2013.01); *A61P 35/00* (2018.01); *A61K 31/519* (2013.01); *C07B 2200/13* (2013.01)

(58) Field of Classification Search
CPC .......................... A61K 31/519; C07D 471/04
USPC ...................... 514/264.11; 544/279
See application file for complete search history.

(56) References Cited

U.S. PATENT DOCUMENTS 7,378,423 B2    5/2008  Kawasaki et al.

FOREIGN PATENT DOCUMENTS

WO    2014066606 A2    5/2014

OTHER PUBLICATIONS

Abe, Hiroyuki et al., "Discovery of a Highly Potent and Selective MEK Inhibitor: GSK1120212 (JTP-74057 DMSO Solvate)", ACS Medicinal Chemistry Letters, vol. 2., Feb. 28, 2011, pp. 320-324.
Russian Patent Office, "International Search Report" in connection with related International Application No. PCT/RU2016/000862, dated Jun. 2, 2017, 2 pgs.

*Primary Examiner* — Jeffrey H Murray
(74) *Attorney, Agent, or Firm* — Kolisch Hartwell, P.C.

(57) ABSTRACT

Novel MEK1, MEK2 and MEK1/2 inhibitors which have lower toxicity in long-term dosage, including the novel compound N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide dimethyl sulfoxide solvate according to formula 1:

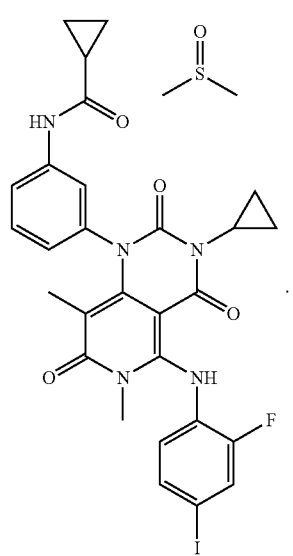

8 Claims, 2 Drawing Sheets

Figure 1:
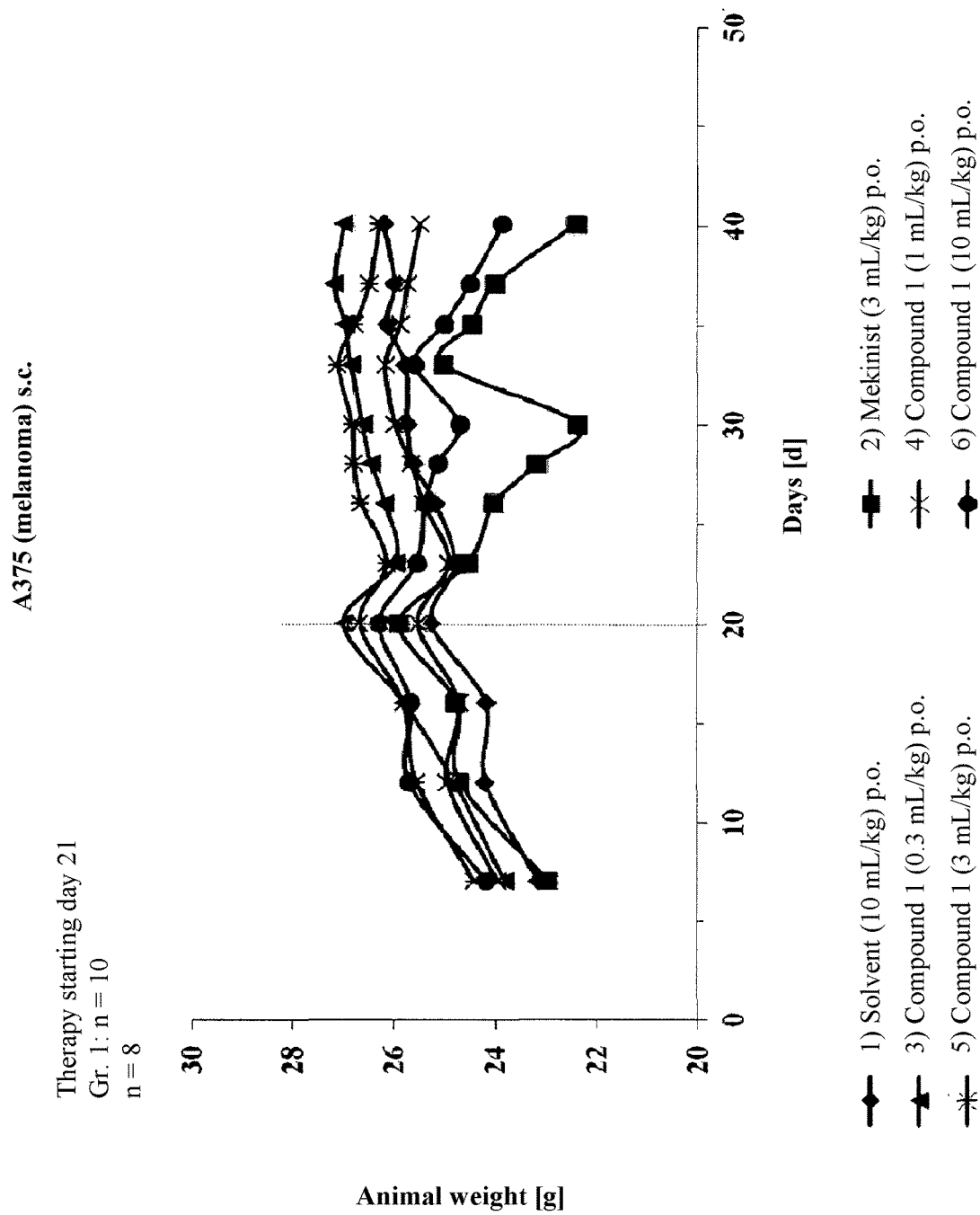

N-{3-[3-CYCLOPROPYL-5-(2-FLUORO-4-IODOPHENYLAMINO)-6,8-DIMETHYL-2,4,7-TRIOXO-3,4,6,7-TETRAHYDRO-2H-PYRIDO[4,3-D]PYRIMIDIN-1-YL]-PHENYL}-CYCLOPROPANECARBOXAMIDE DIMETHYL SULFOXIDE SOLVATE AS AN MEK1/2 INHIBITOR

TECHNICAL FIELD

This invention relates to new derivatives of pyrido[4,3-d]pyrimidine-2,4,7-trione, namely N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide dimethyl sulfoxide solvate, which is interesting as a drug for treatment of disorders caused by adverse cell proliferation, particularly as antitumor agent. More specifically, this invention relates to MEK1, MEK2 and ME1/2 inhibitor interesting as antitumor drug, which may be used for treatment of malignant melanomas.

BACKGROUND ART

There are well-known MEK1, MEK2 and MEK1/2 inhibitors, which structure includes 1H,6H-pyrido[4,3-d]pyrimidine-2,4,7-trione [WO 2005/121142, WO 2012/088033, USA 7378423], the most advanced drug being Mekinist (Trametinib dimethyl sulfoxide, GSK1120212) [H. Abe, S. Kikuchi, K. Hayakawa et al. ACS Med. Chem. Lett. 2011, 2, 320-324]. GSK1120212 is efficient MEK1/2 inhibitor, which shows higher efficiency against u-MEK1/2 prior to C-Raf activation (u-MEK1: $IC_{50}$=0.7 nM) as compared to pre-activated one (pp-MEK 1: IC50=14.9 nM) [http://clincancerres.aacrjournals.org/content/17/5/989.full].

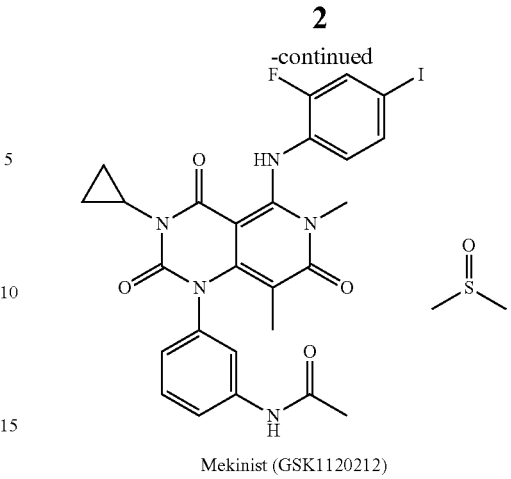

Trametinib

Mekinist (GSK1120212)

However, Trametinib and Mekinist are practically insoluble in aqueous media between pH=2 and pH=8. Trametinib and Mekinist are also very slightly soluble in organic solvents including highly polar ones (sparingly soluble in hot aprotic solvents).

This is why compounds, which may demonstrate favorable efficiency profiles with regard to MEK 1, MEK 2 and MEK 1/2, and high solubility in aqueous or organic solvents, are still in demand. Due to improved bioavailability these compounds are expected to be more suitable as cancer therapeutic agents.

Besides that, although Mekinist has low single-dose oral toxicity ($LD_{50}$>2000 mg/kg for mice), critical weight loss or sometimes even animal deaths are observed during long-term high dose level administration. Thus, a search of lower long-term dosage toxicity products of this group remains very important.

The aim of the present invention is to create novel MEK1, MEK2 and MEK1/2 inhibitors which have lower toxicity in long-term dosage.

This aim is achieved by the novel compound N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide dimethyl sulfoxide solvate of formula 1.

Invention Disclosure

The applicants unexpectedly found that the novel compound N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide dimethyl sulfoxide solvate of formula 1 is comparable with Trametinib in efficiency to MEK1, MEK2 and MEK1/2 being non-toxic in long-term dosage.

Therefore, the novel compound N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide dimethyl sulfoxide solvate of formula 1 can be particularly useful in treatment of disorders involving MEK1, MEK2 and MEK1/2, e.g. in treatment of cancer including malignant melanomas.

The subject of this invention is N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide dimethyl sulfoxide solvate of formula 1.

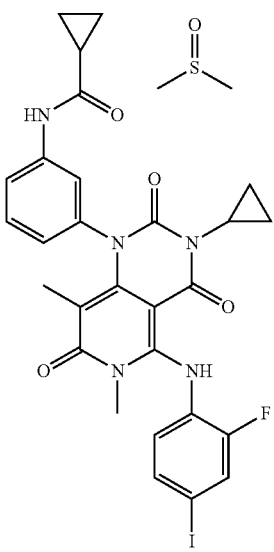

1

The subject of this invention is also MEK1, MEK2 and MEK1/2 inhibitor comprising the compound of formula 1.

The advantage of the novel compound of formula 1 is higher solubility in organic media, which may provide a wider variety of suitable formulations and enable a higher bioavailability and other pharmacokinetic parameters. Thus, for example, solubility of the compound of formula 1 in dimethyl sulfoxide is more than 2 times greater than that of Trametinib. Solubility in a mixture of 4% dimethyl sulfoxide and 96% vegetable oil is higher as well. Solubility of the compound of formula 1 in various media as compared to that of Trametinib are given in Table 1.

TABLE 1

Solubility of the compound of formula 1 and Trametinib in various media

| Compound | Solubility in water (mg/mL) | Solubility in dimethyl sulfoxide (mg/mL) | Solubility in a mixture of 4% sulfoxide and 96% corn oil (mg/mL) |
| --- | --- | --- | --- |
| Compound of formula 1 | <1 | 47 | 7 |
| Trametinib | <1 | 22 | 3 |

Inhibiting activity of the novel compound of formula 1 is comparable to inhibiting activity of Trametinib with regard to MEK1, the experimental value being $IC_{50}=8.02$ nM ($IC_{50}=8.14$ nM for Trametinib).

Significantly lower course dosage toxicity as compared to the prototype (Mekinist, dimethyl sulfoxide complex of Trametinib) is absolute advantage of the novel compound of formula 1. Efficiency studies on A375 human melanoma xenograft model showed that the compound of formula 1 inhibits tumor growth and causes tumor regression in a dose-dependent manner. Efficiency of the compound of formula 1 is comparable with that of Mekinist, the compound of formula 1 being less toxic: experimental treatment by Mekinist resulted in a critical weight loss and death of two animals, while the compound of formula 1 did not cause animal deaths even in higher doses.

Antitumor activity study of the compound of formula 1 vs Mekinist was carried out on NMRI nude female mice. After formation of tumors the animals were subdivided into groups so that average tumor size in the group was ~150 $mM^3$. The animals were treated with the test products for 21 days. Weights of the animals in experimental groups received the compound of formula 1 in doses up to and including 3 mg/kg were not significantly different from those of the animals in control group (FIG. 1). Treatment by 10 mg/kg dose of the compound of formula 1 resulted in animal body weight loss, which was observed throughout the study from the first administration, but was not more than 20% as compared to the treatment start date. However, intragastric administration of 3 mg/kg of Mekinist for 9 days resulted in a critical body weight loss and death of two animals that caused the need to stop treatment in this group for 3 days to restore the weight.

Figure 2:
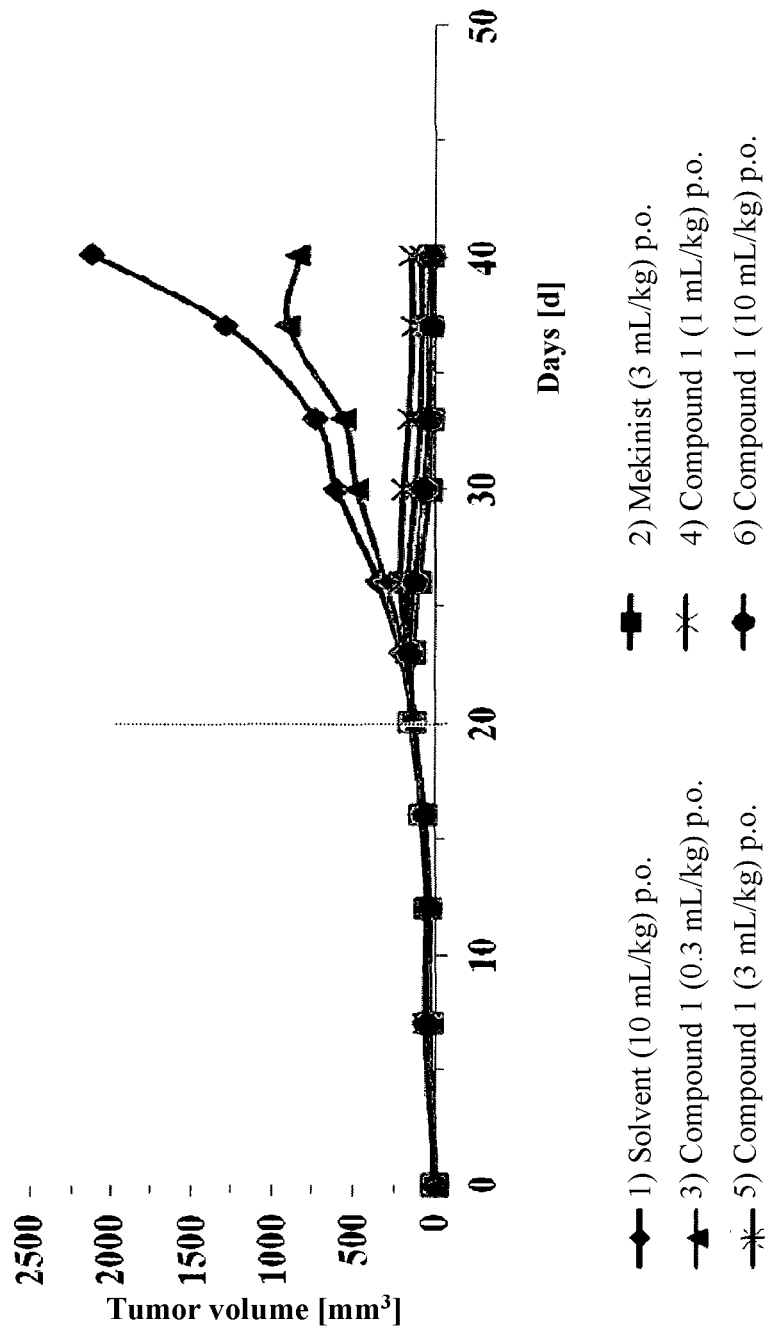

Dynamics of tumor growth is shown in FIG. 2. Intragastric administration of 0.3 mg/kg of the compound of formula 1 had no effect on tumor growth, while a significant inhibition of tumor growth was observed in all other groups. Also, tumor regression was observed in three of eight animals received 1 mg/kg of the compound of formula 1, and in 7/8 and 8/8 animals received 3 and 10 mg/kg of the compound of formula 1, respectively. Intragastric administration of 3 mg/kg of Mekinist caused regression in 100% animals in the group as well.

Thus, the compound of formula 1 exhibited dose-dependent tumor growth inhibition and regression, did not cause animal death and moderately reduced animals weight in a maximum studied dose only.

The subject of this invention is also MEK1, MEK2 and MEK1/2 inhibitor comprising the compound of formula 1. This inhibitor is preferably used for treatment of cancer including malignant melanomas in patient.

The subject of this invention is also a method of production of the compound of formula 1, which consists in interaction of 1-(3-aminophenyl)-3-cyclopropyl-5-{(2-fluoro-4-iodophenyl)amino}-6,8-dimethylpyrido[4,3-d]pyrimidine-2,4,7(1H,3H,6H)-trione of formula 2 or its salt with cyclopropylcarboxylic acid or its activated derivative (e.g., chloroanhydride or respective activated ester or anhydride of this acid) in a solvent, e.g., $CH_2Cl_2$, tetrahydrofuran, N,N-dimethylformamide, N,N-dimethylacetamide or N-methylpyrrolidone with further obtaining a crystalline solvate of the finished product by slow cooling of a hot saturated solution in dimethyl sulfoxide.

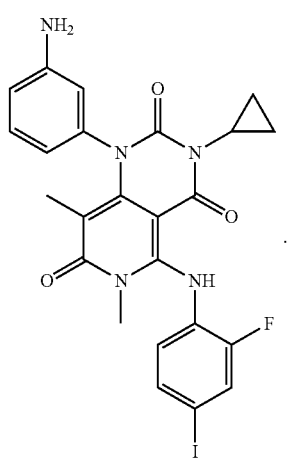

2

The subject of this invention is active ingredient for preparation of pharmaceutical compositions and dosage forms comprising the compound of formula 1.

The subject of this invention is pharmaceutical composition exhibiting MEK1, MEK2 and MEK1/2 inhibitor properties and containing therapeutically effective quantity of the compound of formula 1 as active ingredient, and pharmaceutically acceptable excipients.

The pharmaceutical composition may be in the form suitable for oral use (e.g., tablets, pastilles, hard or soft capsules, aqueous or oily suspensions, emulsions, dispersible powders or granules, syrups or elixirs), for topical use (e.g., creams, ointments, gels, aqueous or oily solutions or suspensions), for inhalations (e.g., fine powder or liquid aerosol), for insufflation (e.g., fine powder) or for parenteral administration (e.g., sterile aqueous or oily solution for intravenous, subcutaneous or intramuscular dose injection, or suppositories for rectal administration).

The pharmaceutical composition may be obtained by usual methods using well-known conventional pharmaceutical excipients. Thus. the pharmaceutical composition intended for oral administration may contain, e.g., one or several colorants, sweeteners, flavors and/or preservative.

Usually the compounds of formula 1 are administered to patient as a single dose of 5-5000 mg/m$^2$ of the body surface area, i.e. about 0.1-100 mg/kg that generally provides therapeutically effective dose. Usually single dosage form, such as tablet or capsule, contains, e.g., 1-250 mg of active ingredient. Daily dose always varies depending on patient, specific administration route and severity of the disorder upon treatment. Therefore, the doctor, which performs treatment of the specific patient, can determine an optimal dose. In this description the term "therapy" includes "prophylaxis".

The compound of formula 1 with inhibiting activity to MEK1, MEK2 and MEK1/2 can be used for treatment of diseases or medical conditions related to MEK1, MEK2 and MEK1/2 activity, e.g., in treatment of cancer. Types of cancer, which may be susceptible to treatment using the compound of formula 1 or its pharmaceutically acceptable salts and/or solvates include (without limitation) malignant melanomas.

The subject of this invention is also a drug for treatment a disease related to MEK1, MEK2 and MEK1/2 including therapeutically effective quantity of the compound of formula 1. One of the versions of this invention is that this drug is intended for treatment of a disease related to MEK1, MEK2 and MEK1/2 and comprising cancer.

The subject of this invention is also a method for treatment a disease related to MEK1, MEK2 and MEK1/2 including the use of the compound of formula 1 as defined above. One of the versions of this invention is treatment of a disease related to MEK1, MEK2 and MEK1/2 and comprising cancer.

In accordance with another aspect of this invention the compound of formula 1 is proposed to be used, as defined above, for preparation of a drug for treatment of cancer by mixing therapeutically effective quantity of the compound of formula 1 with pharmaceutically acceptable excipient.

In accordance with another aspect of this invention a method of obtaining anticancer effect in patient needing such treatment was also proposed, which includes administration of effective quantity of the compound of formula 1 to the patient.

In accordance with another aspect of this invention a method of treatment of a person suffering a disease in which MEK1/2 inhibition is useful was also proposed; the method includes steps of administration of effective quantity of the compound of formula 1 to the patient needing such treatment. Particularly, the disease in which MEK1, MEK2 and MEK1/2 inhibition is useful is cancer.

In any of aspects or versions mentioned herein, where cancer is indicated in a general sense, the said cancer may be selected from brain tumor (neuroglioma with a component of malignant astroglioma and oligodendrogliomas, etc.), esophageal cancer, stomach cancer, liver cancer, pancreatic cancer, colorectal cancer (colon cancer, rectal cancer, etc.), lung cancer (non-small cell lung cancer, small cell lung cancer, primary and metastatic cancer squamous cells, etc.), kidney cancer, breast cancer, ovarian cancer, prostate cancer, skin cancer, neuroblastoma, sarcoma, osteochondroma, osteoma, osteosarcoma, seminoma, extragonadal tumors, testicular tumor, uterine cancer (cervical cancer, endometrial cancer, etc.), head cancer and neck tumor (maxillary sinus, laryngeal cancer, pharyngeal cancer, tongue cancer, intraoral cancer, etc.), multiple myeloma, malignant lymphoma (reticulosarcoma, lymphosarcoma, Hodgkin's disease, etc.), true polycythemia, leukemia (acute myeloid leukemia, chronic myeloid leukemia, acute lymphocytic leukemia, chronic lymphocytic leukemia, etc.), goiter, pelvic cancer, ureteral tumor, bladder tumor, gallbladder cancer, bile duct cancer, malignant melanoma, pediatric tumor (Ewing's sarcoma, Wilms' tumor, rhabdomyosarcoma, vascular sarcoma, embryonal testicular cancer, neuroblastoma, retinoblastoma, hepatoblastoma, nephroblastoma, etc.) and such things.

Treatment of cancer diseases described above may be used as monotherapy or may include general surgery or radiation therapy, or chemotherapy, or immunotherapy in addition to the compound according to this invention. This chemotherapy may be introduced simultaneously, successively or separately, and may additionally include one or more antitumor agents from the following categories: antiproliferative/anticancer drugs and their combinations used in medical oncology; cytostatic agents; anti-invasion agents; growth factor inhibitors; antiangiogenic agents; vascular agents; damaging endothelin receptor antagonists; antisense therapies; gene therapy approaches; and immunotherapy approaches (J).

Thus, this invention proposes a pharmaceutical composition including the compound of formula 1 and additional antitumor substance, as defined above, for concomitant treatment of cancer.

This invention proposes a pharmaceutical composition including the compound of formula 1 and additional antitumor substance, as defined above, for combined treatment of cancer.

The term "concomitant treatment" used in relation to combined therapy should be read as simultaneous, separate or successive administration.

The invention proposes the use of the compound of formula 1 and additional antitumor substance for concomitant treatment of cancer.

This invention is supported by drawings.

FIG. 1. Dynamics of animal body weight change during treatment by the drugs under study.

FIG. 2. Dynamics of A375 human melanoma tumor growth in xenograft model during Mekinist and the compound of formula 1 treatment.

THE BEST IMPLEMENTATION OF THE INVENTION

This invention will be described in more details using specific examples. The following examples are provided as illustrations and not intended for any limitation of the invention. Experts in this field of art can easily understand various noncritical parameters, which may be changed or modified to give essentially the same results.

Example 1. Method of Preparation of N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecarboxamide Dimethyl Sulfoxide Solvate Add cyclopropylcarbonyl chloride (182 mg, 1.74 mmol) to the solution of 1-(3-aminophenyl)-3-cyclopropyl-5-{(2-fluoro-4-iodophenyl)amino}-6,8-dimethylpyrido[4,3-d]pyrimi-dine-2,4,7(1H,3H,6H)-trione of formula 2 (500 mg, 0.87 mmol) and diisopropylethylamine (225 mg, 1.74 mmol) in 5 mL of dimethylformamide at ambient temperature and mix the reaction mass overnight. Upon completion of the reaction evaporate the solvent under vacuum, dissolve the residue in 5 mL of dichloromethane and wash successively with sodium hydrogen carbonate saturated aqueous solution and sodium chloride saturated aqueous solution. Separate organic layer and dry over anhydrous sodium sulfate overnight, filter and evaporate the filtrate under vacuum. Isolate the product by silica gel flash chromatography using dichloromethane and a mixture of dichloromethane and ethyl acetate (1:1) as effluent. Dissolve crude product (250 mg) in 1.3 mL of dimethyl sulfoxide at 70° C. and mix the solution for 1 hour, then cool to ambient temperature and mix overnight. Filter the precipitate, wash with dichloromethane on the filter and dry under high vacuum at 40-50° C. for 2 hours. Obtain N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-cyclopropanecar boxamide dimethyl sulfoxide solvate (130 mg, 48%) as a white crystalline powder.

$^1$H NMR (CDCl$_3$, 400 MHz): 0.79 (m, 2H), 0.86 (m, 2H), 1.05-1.15 (m, 4H), 1.44 (s, 3H), 1.5 (m, 1H), 2.62 (s, 6H), 2.74 (m, 1H), 3.21 (s, 3H), 6.7 (t, 1H), 7.03 (m, 1H), 7.31-7.4 (m, 2H), 7.45 (d, 1H), 7.53 (d, 1H), 7.65 (s, 1H), 7.71 (s, 1H), 11.3 (s, 1H).

Example 2

Determination of thermodynamic solubility of the compound of formula 1 and Trametinib prototype. Mix 5 mg of the compound under study with 1 mL of universal buffer (Pion Ltd), pH=2.0; 4.0 or 7.0 for 15 min at 25° C. Use additional quantities of the substances until the solution becomes turbid. Incubate vials with the solution for 24 h at 25° C. with mixing to achieve equilibrium between saturated solution and precipitate. Upon equilibration filter 200 µL of the solution (in duplicate) through a 96-well filter plate (Millipore) to separate the precipitate. Determine concentrations of the compounds in the filtrate by spectrophotometry using standard calibration curve. Carry out measurement of optical absorption spectrum of the substance and plot calibration curve at the selected wavelength (usually corresponding to the substance absorption maximum $\lambda_{max}$). Calculate concentration of the substance in the filtrate (i.e., solubility) by the following equation:

$$\text{Solubility}=(OD_{\lambda max} \text{ filtrate}-OD_{\lambda max} \text{ blank})/\text{Slope} \times 1.67 \times \text{Filtrate dilution},$$

where:
$OD_{\lambda max}$ filtrate=absorbance of the filtrate:
$OD_{\lambda max}$ blank=absorbance of the blank solution without the substance;
Slope=slope of the calibration curve;
1.67=dilution factor for the filtrate in acetonitrile;
Filtrate dilution=dilution factor for the filtrate in the buffer.

The results are shown in Table 1.

Example 3

Assay. The substances were tested for the effect on MEK1 kinase activity using Z'-LYTE screening platform (Life Technologies). Concentration of DMSO in the reaction mixture was 1%. Dilute 100 nL of 100-fold sinks of the substances under study in 100% DMSO in 2.4 µL of kinase buffer (50 mM of HEPES pH 7.5, 0.01% BRIJ-35, 10 mM of mgCl$_2$, 1 mM of EGTA) and add to 5 µL of 2-fold Substrate/Kinase mixture (MEK1/inactivated MARK1 (ERK2)/Ser/Thr03, final content 0.08-0.31 ng of MEK1, 105 ng of inactivated MARK1 (ERK2), and 2 µM of Ser/Thr03) in 384-well plate (black, small-volume manufactured by Corning, кат. #3676). Pre-incubate the substances with kinases for 10 min at ambient temperature. After that add 2.5 µL of 4-fold ATP solution to start the reaction (final concentration of ATP in the reaction mixture is 100 µM). After 30 sec of incubation on a shaker incubate the reaction for 60 min at ambient temperature. Then add 5 µL of Reagent B (Life Technologies) diluted as 1:1024 and incubate for 60 min more at ambient temperature. Measure fluorescence with excitation at 400 nM and emission at 445 nM and 520 nM. Calculate degree of phosphorylation of the peptide substrate by the equation below (low emission ratio means that the peptide is phosphorylated, i.e. kinase activity is not inhibited and high emission ratio means that the peptide is not phosphorylated, i.e. kinase activity is inhibited).

Calculate % phosphorylation as follows:

$$\left\{ 1 - \frac{(EmissionRatio \times F_{100\%}) - C_{100\%}}{(C_{0\%} - C_{100\%}) + [EmissionRatio \times (F_{100\%} - F_{0\%})]} \right\} * 100,$$

Calculate % inhibition as follows:

$$\left\{ 1 - \frac{\%Phos_{Sample}}{\%Phos_{0\% \, InhibitionCtl}} \right\} * 100,$$

where:
$C_{100\%}$=average coumarin emission signal, 100% phosphorylation control;
$C_{0\%}$=average coumarin emission signal, 0% phosphorylation control;
$F_{100\%}$=average fluorescein emission signal, 100% phosphorylation control;
$F_{0\%}$=average fluorescein emission signal, 0% phosphorylation control.

Example 4

Study of efficiency in human melanoma xenograft model. The study was carried out in ProQinase GmbH Freiburg, Breisacher Str. 117, D-79106 Freiburg, GERMANY.

A375 human melanoma cells were cultivated in vials with DMEM medium with addition of 10% FBS in a humid atmosphere containing 95% of air and 5% of $CO_2$ at 37° C. Cancer cells were passaged to animals after an adaptation period. For that end the cells were collected using TrypLE Express (Invitrogen), washed and suspended in sterile PBS to the final concentration of $3 \times 10^7$ cells/mL. This cell suspension was injected subcutaneously (SC) in mice left flanks ($3 \times 10^6$ cells or 100 µL per mouse).

When average tumor size reached 100-200 $mM^3$ the animals were subdivided into experimental groups and treatment with the test drugs was started. The products were administered intragastrically daily, while the control group received the solvent. Experimental product doses are presented in Table 2.

TABLE 2

Product doses in the study of efficiency in human melanoma xenograft model

| Group | Substances | Dose, mg/kg | Number of animals |
|---|---|---|---|
| 1 | Solvent | 10 mL/kg | 10 |
| 2 | Mekinist | 3.0 | 8 |
| 3 | Compound of formula 1 | 0.1 | 8 |
| 4 | Compound of formula 1 | 0.3 | 8 |
| 5 | Compound of formula 1 | 1.0 | 8 |
| 6 | Compound of formula 1 | 3.0 | 8 |
| 7 | Compound of formula 1 | 10.0 | 8 |

Key Measured Parameters:

Measurement of subcutaneously implanted tumors was carried out 2 times a week starting from the day of cells introduction. Tumor volume ($mm^3$) was determined by the equation:

$$V = L \times W^2 / 2,$$

where L corresponds to maximum and W to minimum tumor diameter (mm). The measurements were carried out using a slide caliper.

The study included calculation of tumor growth inhibition values:

$$T/C = V_{exp}/V_{ctrl} \times 100\%,$$

where:

$V_{ctrl}$ = average tumor volume in the control group;

$V_{exp}$ = average tumor volume in the experimental group.

Also, health and behavior of animals were monitored, numbers of lethal outcomes and tumor regressions were recorded:

$$\text{Regression} = (V_{ini} - V_{fin})/V_i \times 100\%,$$

where:

$V_{ini}$ = initial tumor volume at the start of treatment;

$V_{fin}$ = tumor volume at the end of treatment.

Measurement of animal weights was carried out 3 times a week.

TABLE 3

Tumor inhibition parameters after 21 days of treatment (T/C)

| Group | Substances | Dose, mg/kg | Number of animals | $V_{avg}$, $mm^3$ | T/C, % |
|---|---|---|---|---|---|
| 1 | Solvent | — | 8 | 2112.0 | |
| 2 | Mekinist | 3.0 | 6 | 21.1 | 1.0 |
| 3 | Compound of formula 1 | 0.3 | 7 | 834.3 | 39.5 |
| 4 | Compound of formula 1 | 1.0 | 7 | 140.5 | 6.7 |
| 5 | Compound of formula 1 | 3.0 | 8 | 84.5 | 4.0 |
| 6 | Compound of formula 1 | 10.0 | 8 | 26.1 | 1.2 |

FIG. 2 shows dynamics of A375 melanoma tumor growth in xenograft model during Mekinist and the compound of formula 1 treatment.

The compound of formula 1 exhibited a dose-dependent tumor growth inhibition and regression comparable to Mekinist effect intensity. However, as distinct from Mekinist, the compound of formula 1 did not cause animal deaths in any of the doses studied (Mekinist treatment resulted in critical weight loss and two animal deaths) and only moderately reduced animal weight in the maximum dose studied. This assumes less toxicity of the compound of formula 1 as compared to Mekinist without loss of melanoma treatment efficiency.

Example 5

Preparation of the drug in tablets. Mix 1600 mg of starch, 1600 mg of ground lactose, 400 mg of talc and 1000 mg of the inhibitor of formula 1, and compress into a bar. Grind this bar into granules and sieve collecting 14-16 mesh granules. Compress these granules into tablets of suitable shapes (500 mg each).

Example 6

Preparation of the drug in capsules. Mix the inhibitor of formula 1 with lactose (2:1). Fill this powder mixture in gelatin capsules of a suitable size (600 mg each).

Example 7

Preparation of the drug as a composition for intramuscular, intraperitoneal or subcutaneous injections. Mix 500 mg of the inhibitor of formula 1 with 300 mg of chlorobutanol, 2 mL of propylene glycol and 100 mL of water for injection. Filter the solution and fill in 1 mL ampoules, which are then sealed.

INDUSTRIAL APPLICABILITY

Experts in this field of art can easily understand various noncritical parameters, which may be changed or modified to give the same results. Various modifications of the invention, in addition to those described herein, would be evident to the experts in this field of art from the description provided above.

The invention claimed is:
1. A compound having a structure according to formula 1:

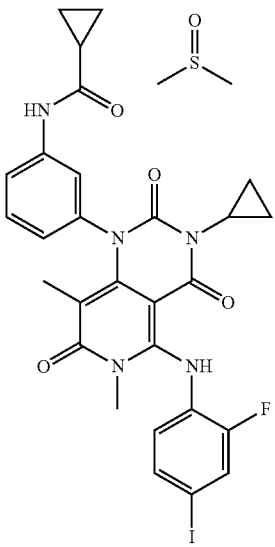

2. A pharmaceutically-acceptable composition comprising the compound of claim 1 as an active ingredient.
3. The pharmaceutically-acceptable composition of claim 2, wherein the active ingredient exhibits inhibitor properties for one or both of MEK1 and MEK2.
4. The pharmaceutically-acceptable composition of claim 2, wherein the active ingredient is present in a therapeutically effective amount.
5. The pharmaceutically-acceptable composition of claim 2, further comprising one or more pharmaceutically acceptable excipients.
6. The pharmaceutically-acceptable composition of claim 2, where the composition is in the form of tablets, capsules, or solutions for injection.
7. The pharmaceutically-acceptable composition of claim 6, where the composition is placed in a pharmaceutically acceptable container.
8. A method of preparing a compound according to claim 1, comprising treating a compound according to formula 2 or its salt, with cyclopropanecarboxylic acid or an activated derivative of cyclopropanecarboxylic acid

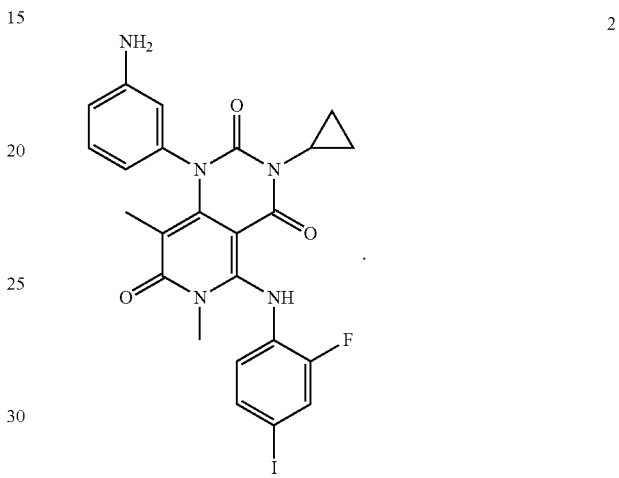

* * * * *